(12) United States Patent
Huynh

(10) Patent No.: US 9,078,659 B2
(45) Date of Patent: Jul. 14, 2015

(54) DELIVERY SYSTEM WITH HOOKS FOR RESHEATHABILITY

(75) Inventor: Andy Huynh, Westminster, CA (US)

(73) Assignee: Covidien LP, Mansfield, MA (US)

(*) Notice: Subject to any disclaimer, the term of this patent is extended or adjusted under 35 U.S.C. 154(b) by 114 days.

(21) Appl. No.: 13/453,047

(22) Filed: Apr. 23, 2012

(65) Prior Publication Data

US 2013/0282099 A1    Oct. 24, 2013

(51) Int. Cl.
| | |
|---|---|
| *A61B 17/12* | (2006.01) |
| *A61F 2/966* | (2013.01) |
| *A61F 2/90* | (2013.01) |
| *A61F 2/95* | (2013.01) |

(52) U.S. Cl.
CPC ............ *A61B 17/12118* (2013.01); *A61F 2/90* (2013.01); *A61F 2/966* (2013.01); *A61B 2017/12054* (2013.01); *A61B 2017/12077* (2013.01); *A61F 2002/9511* (2013.01); *A61F 2002/9534* (2013.01); *A61F 2002/9665* (2013.01)

(58) Field of Classification Search
CPC ... A61F 2/90; A61F 2/966; A61F 2002/9511; A61F 2002/9534; A61B 17/12118; A61B 2017/12077; A61B 2017/12054; A61B 2002/9511; A61B 2002/9534; A61B 2002/9665
USPC ........ 606/108, 191, 194, 200; 623/1.11, 1.12, 623/1.16, 1.18
See application file for complete search history.

(56) References Cited

U.S. PATENT DOCUMENTS

| | | | |
|---|---|---|---|
| 4,655,771 A | 4/1987 | Wallsten | |
| 4,723,936 A | 2/1988 | Buchbinder et al. | |
| 4,990,151 A | 2/1991 | Wallsten | |
| 5,026,377 A | 6/1991 | Burton et al. | |
| 5,445,646 A | 8/1995 | Euteneuer et al. | |
| 5,474,563 A * | 12/1995 | Myler et al. | ............ 606/108 |
| 5,545,209 A | 8/1996 | Roberts et al. | |

(Continued)

FOREIGN PATENT DOCUMENTS

| | | |
|---|---|---|
| EP | 775470 A1 | 5/1997 |
| EP | 1637176 A1 | 3/2006 |

(Continued)

OTHER PUBLICATIONS

U.S. Appl. No. 13/553,855, filed Jul. 20, 2012.

(Continued)

*Primary Examiner* — Julian W Woo
*Assistant Examiner* — Lucas Paez
(74) *Attorney, Agent, or Firm* — Mark J. Kertz, Esq.

(57) ABSTRACT

Described herein are flexible implantable devices or stents that can, for example, navigate the tortuous vessels of the neurovasculature. The devices can also conform to the shape of tortuous vessels of the vasculature. In some embodiments, the devices can direct blood flow within a vessel away from an aneurysm or limit blood flow to the aneurysm. Methods and structures are provided for adjusting, along a length of the device, the porosity of the device while maintaining a cross-sectional dimension. In some embodiments, small hooks releasably engage the stent at a proximal end and are able to resheath the stent by retracting a proximal retaining member where the hooks are coupled to. The hooks straighten, unfurl, or otherwise disengage the stent when either unrestrained by a catheter or when coming into contact with an external stimulus found in the patient's vasculature.

25 Claims, 4 Drawing Sheets

(56) References Cited

U.S. PATENT DOCUMENTS

| | | | |
|---|---|---|---|
| 5,571,135 A | 11/1996 | Fraser et al. |
| 5,636,641 A | 6/1997 | Fariabi |
| 5,702,418 A | 12/1997 | Ravenscroft |
| 5,725,571 A | 3/1998 | Imbert et al. |
| 5,776,141 A | 7/1998 | Klein et al. |
| 5,824,041 A | 10/1998 | Lenker et al. |
| 5,935,161 A | 8/1999 | Robinson et al. |
| 5,968,053 A | 10/1999 | Revelas |
| 6,077,295 A | 6/2000 | Limon et al. |
| 6,077,297 A | 6/2000 | Robinson et al. |
| 6,126,685 A | 10/2000 | Lenker et al. |
| 6,149,680 A | 11/2000 | Shelso et al. |
| 6,193,739 B1 | 2/2001 | Chevillon et al. |
| 6,251,132 B1 | 6/2001 | Ravenscroft et al. |
| 6,264,683 B1 | 7/2001 | Stack et al. |
| 6,350,278 B1 | 2/2002 | Lenker et al. |
| 6,371,953 B1 * | 4/2002 | Beyar et al. | 623/1.1 |
| 6,383,171 B1 | 5/2002 | Gifford et al. |
| 6,395,008 B1 | 5/2002 | Ellis |
| 6,395,017 B1 | 5/2002 | Dwyer et al. |
| 6,419,693 B1 | 7/2002 | Fariabi |
| 6,425,898 B1 | 7/2002 | Wilson et al. |
| 6,428,552 B1 | 8/2002 | Sparks |
| 6,443,971 B1 | 9/2002 | Boylan et al. |
| 6,468,298 B1 | 10/2002 | Pelton |
| 6,517,547 B1 | 2/2003 | Feeser et al. |
| 6,562,063 B1 | 5/2003 | Euteneuer et al. |
| 6,576,006 B2 | 6/2003 | Limon et al. |
| 6,582,460 B1 * | 6/2003 | Cryer | 623/1.11 |
| 6,602,271 B2 | 8/2003 | Adams et al. |
| 6,699,274 B2 | 3/2004 | Stinson |
| 6,706,055 B2 | 3/2004 | Douk et al. |
| 6,764,504 B2 | 7/2004 | Wang et al. |
| 6,808,529 B2 | 10/2004 | Fulkerson |
| 6,815,325 B2 | 11/2004 | Ishii |
| 6,830,575 B2 | 12/2004 | Stenzel et al. |
| 6,843,802 B1 | 1/2005 | Villalobos et al. |
| 6,866,679 B2 | 3/2005 | Kusleika |
| 6,932,837 B2 | 8/2005 | Amplatz et al. |
| 6,960,227 B2 | 11/2005 | Jones et al. |
| 6,989,024 B2 | 1/2006 | Hebert et al. |
| 7,001,422 B2 | 2/2006 | Escamilla et al. |
| 7,011,675 B2 | 3/2006 | Hemerick et al. |
| 7,074,236 B2 | 7/2006 | Rabkin et al. |
| 7,147,656 B2 | 12/2006 | Andreas et al. |
| 7,306,624 B2 | 12/2007 | Yodfat et al. |
| 7,357,812 B2 | 4/2008 | Andreas et al. |
| 7,371,248 B2 | 5/2008 | Dapolito et al. |
| 7,427,288 B2 | 9/2008 | Sater |
| 7,473,271 B2 | 1/2009 | Gunderson |
| 7,473,272 B2 | 1/2009 | Pryor |
| 7,572,290 B2 | 8/2009 | Yodfat et al. |
| 7,651,520 B2 | 1/2010 | Fischell et al. |
| 7,655,031 B2 | 2/2010 | Tenne et al. |
| 7,691,138 B2 | 4/2010 | Stenzel et al. |
| 7,867,267 B2 | 1/2011 | Sullivan et al. |
| 7,942,925 B2 | 5/2011 | Yodfat et al. |
| 7,955,370 B2 | 6/2011 | Gunderson |
| 7,981,148 B2 * | 7/2011 | Aguilar et al. | 623/1.11 |
| 7,993,385 B2 | 8/2011 | Levine et al. |
| 8,025,692 B2 | 9/2011 | Feeser |
| 8,034,095 B2 | 10/2011 | Randolph et al. |
| 8,042,720 B2 | 10/2011 | Shifrin et al. |
| 8,066,754 B2 | 11/2011 | Malewicz |
| 8,092,508 B2 | 1/2012 | Leynov et al. |
| 8,133,266 B2 | 3/2012 | Thomas et al. |
| 8,147,534 B2 | 4/2012 | Berez et al. |
| 8,317,850 B2 | 11/2012 | Kusleika |
| 8,790,387 B2 | 7/2014 | Nguyen et al. |
| 2002/0029046 A1 | 3/2002 | Lorentzen Cornelius et al. |
| 2002/0138128 A1 | 9/2002 | Stiger et al. |
| 2003/0050600 A1 | 3/2003 | Ressemann et al. |
| 2004/0024416 A1 | 2/2004 | Yodfat et al. |
| 2004/0220585 A1 * | 11/2004 | Nikolchev | 606/108 |
| 2005/0125051 A1 | 6/2005 | Eidenschink et al. |
| 2005/0143773 A1 | 6/2005 | Abrams et al. |
| 2006/0058865 A1 | 3/2006 | Case et al. |
| 2006/0074477 A1 | 4/2006 | Berthiaume et al. |
| 2006/0184226 A1 | 8/2006 | Austin |
| 2006/0212042 A1 | 9/2006 | Lamport et al. |
| 2007/0027520 A1 | 2/2007 | Sherburne |
| 2007/0078504 A1 | 4/2007 | Mialhe |
| 2007/0088323 A1 | 4/2007 | Campbell et al. |
| 2007/0117645 A1 | 5/2007 | Nakashima |
| 2007/0203563 A1 | 8/2007 | Hebert et al. |
| 2007/0239254 A1 | 10/2007 | Chia et al. |
| 2007/0255388 A1 | 11/2007 | Rudakov et al. |
| 2008/0027528 A1 | 1/2008 | Jagger et al. |
| 2008/0033528 A1 | 2/2008 | Satasiya et al. |
| 2008/0077229 A1 | 3/2008 | Andreas et al. |
| 2008/0140180 A1 | 6/2008 | Dolan et al. |
| 2008/0147162 A1 | 6/2008 | Andreas et al. |
| 2008/0234795 A1 | 9/2008 | Snow et al. |
| 2008/0243225 A1 | 10/2008 | Satasiya et al. |
| 2008/0255653 A1 | 10/2008 | Schkolnik |
| 2008/0300667 A1 | 12/2008 | Hebert et al. |
| 2009/0082609 A1 | 3/2009 | Condado |
| 2009/0105802 A1 | 4/2009 | Henry et al. |
| 2009/0132019 A1 | 5/2009 | Duffy et al. |
| 2009/0143849 A1 | 6/2009 | Ozawa et al. |
| 2009/0157048 A1 | 6/2009 | Sutermeister et al. |
| 2009/0204196 A1 | 8/2009 | Weber |
| 2009/0264985 A1 | 10/2009 | Bruszewski |
| 2009/0287292 A1 | 11/2009 | Becking et al. |
| 2009/0299449 A1 | 12/2009 | Styrc |
| 2009/0318947 A1 | 12/2009 | Garcia et al. |
| 2010/0049293 A1 | 2/2010 | Zukowski et al. |
| 2010/0049297 A1 | 2/2010 | Dorn |
| 2010/0057185 A1 | 3/2010 | Melsheimer et al. |
| 2010/0069852 A1 | 3/2010 | Kelley |
| 2010/0087913 A1 | 4/2010 | Rabkin et al. |
| 2010/0094394 A1 | 4/2010 | Beach et al. |
| 2010/0204770 A1 | 8/2010 | Mas et al. |
| 2010/0262157 A1 * | 10/2010 | Silver et al. | 606/108 |
| 2010/0268328 A1 | 10/2010 | Stiger |
| 2010/0274270 A1 | 10/2010 | Patel et al. |
| 2010/0298931 A1 | 11/2010 | Quadri et al. |
| 2010/0331951 A1 | 12/2010 | Bei et al. |
| 2011/0009943 A1 | 1/2011 | Paul et al. |
| 2011/0022157 A1 | 1/2011 | Essinger et al. |
| 2011/0029065 A1 | 2/2011 | Wood et al. |
| 2011/0034987 A1 | 2/2011 | Kennedy |
| 2011/0054586 A1 | 3/2011 | Mayberry et al. |
| 2011/0093055 A1 | 4/2011 | Kujawski |
| 2011/0098804 A1 | 4/2011 | Yeung et al. |
| 2011/0106235 A1 | 5/2011 | Haverkost et al. |
| 2011/0112623 A1 | 5/2011 | Schatz |
| 2011/0178588 A1 | 7/2011 | Haselby |
| 2011/0190862 A1 | 8/2011 | Bashiri et al. |
| 2011/0190865 A1 * | 8/2011 | McHugo et al. | 623/1.11 |
| 2011/0319904 A1 | 12/2011 | Hollett et al. |
| 2012/0029607 A1 | 2/2012 | McHugo et al. |
| 2012/0035700 A1 | 2/2012 | Leanna et al. |
| 2012/0053681 A1 | 3/2012 | Alkhatib et al. |
| 2012/0059449 A1 | 3/2012 | Dorn et al. |
| 2012/0253447 A1 | 10/2012 | Hayasaka et al. |
| 2013/0085562 A1 | 4/2013 | Rincon et al. |

FOREIGN PATENT DOCUMENTS

| | | |
|---|---|---|
| EP | 1656963 A1 | 5/2006 |
| EP | 2 078 512 | 7/2009 |
| GB | 2179258 A | 3/1987 |
| WO | WO-96/01591 | 1/1996 |
| WO | WO-01/49212 | 7/2001 |
| WO | WO-01/89619 | 11/2001 |
| WO | WO-2007/117645 A2 | 10/2007 |
| WO | WO-2010/127838 A2 | 11/2010 |
| WO | WO-2011/076408 | 6/2011 |
| WO | WO-2011/095966 | 8/2011 |
| WO | WO-2012/040240 | 3/2012 |
| WO | WO-2012/158152 A1 | 11/2012 |

(56) References Cited

OTHER PUBLICATIONS

U.S. Appl. No. 13/614,349, filed Sep. 13, 2012.
U.S. Appl. No. 13/692,021, filed Dec. 3, 2012.
U.S. Appl. No. 13/614,035, filed Sep. 13, 2012.
U.S. Appl. No. 13/664,547, filed Oct. 31, 2012.

* cited by examiner

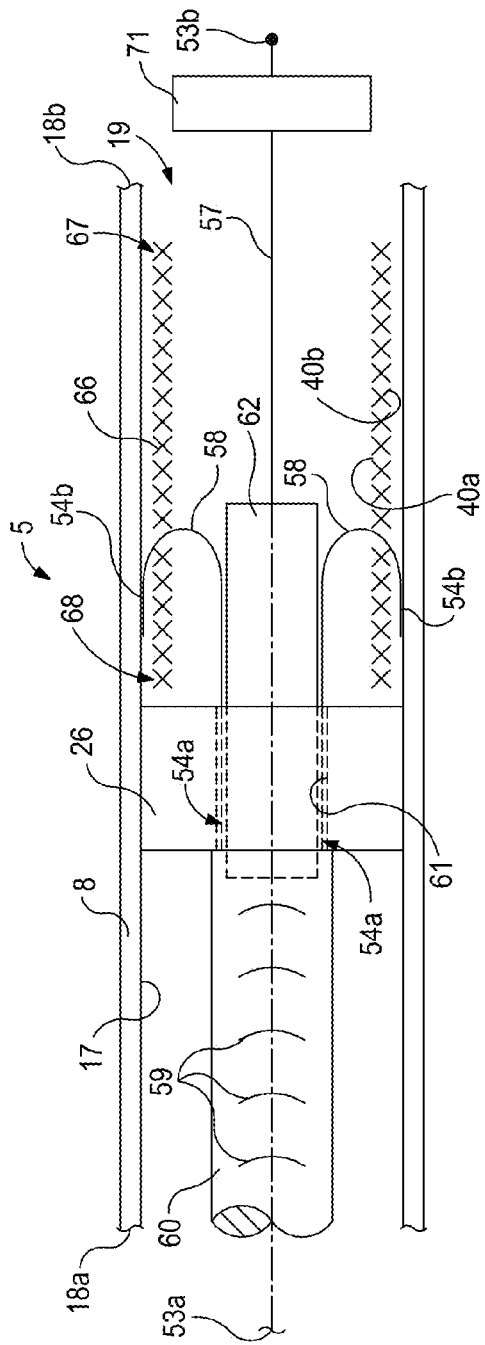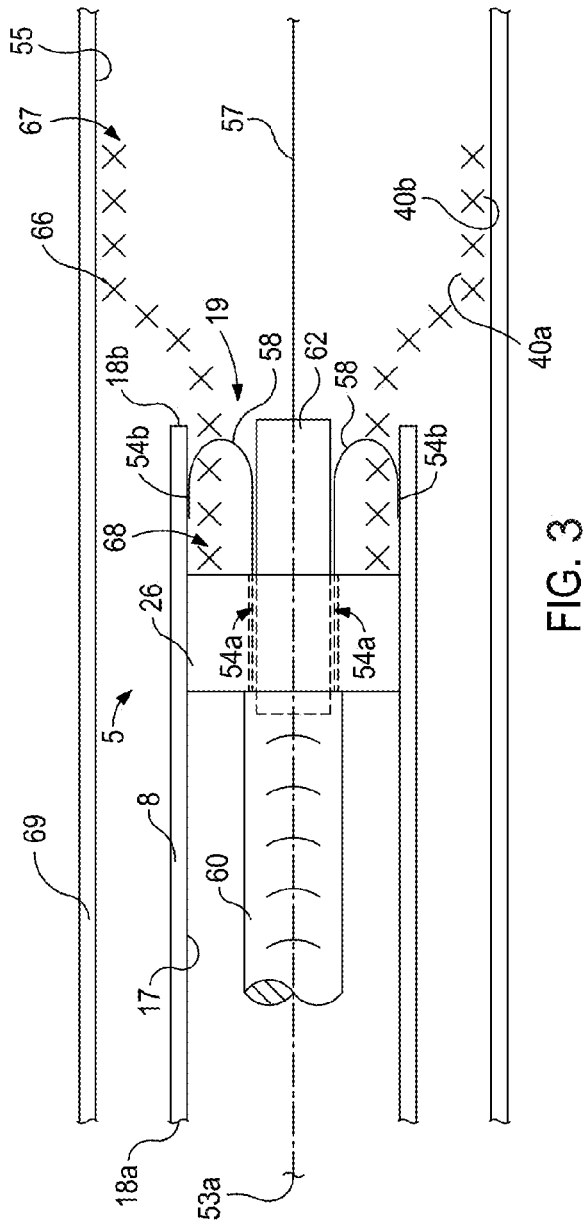

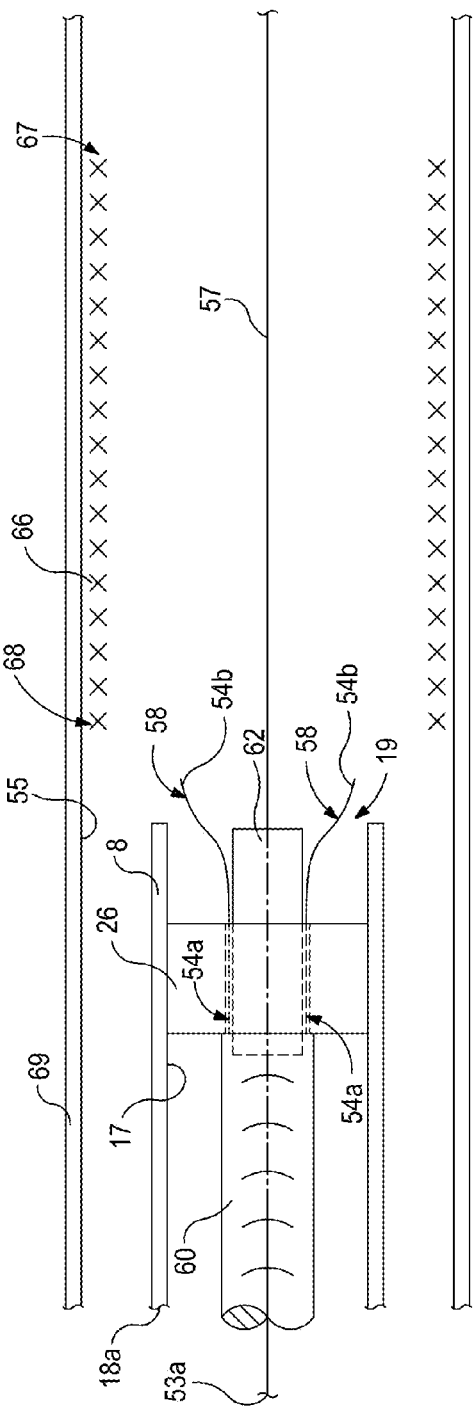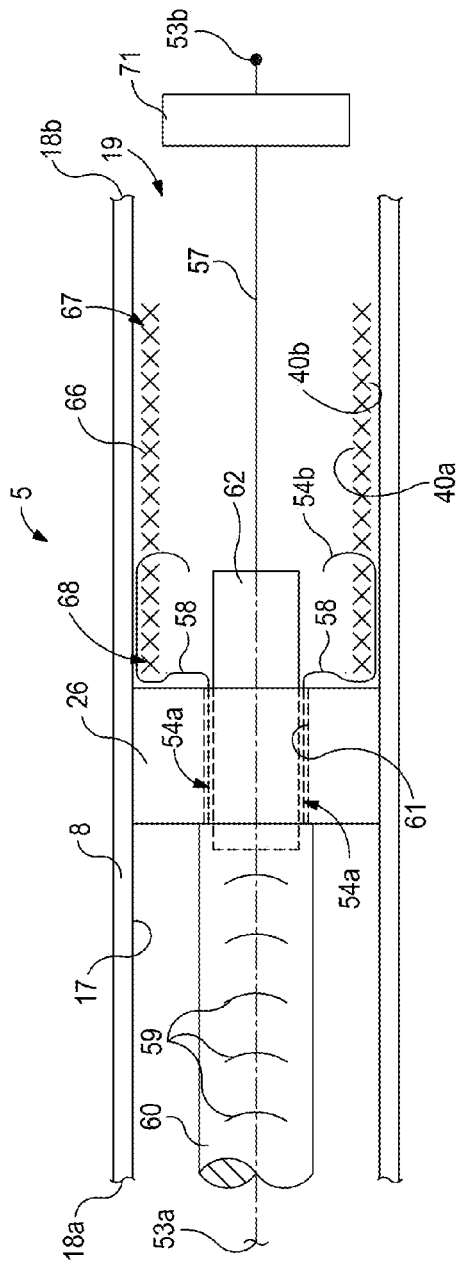

DELIVERY SYSTEM WITH HOOKS FOR RESHEATHABILITY

FIELD OF THE INVENTION

The present application generally relates to implantable devices for use within a patient's body and, more particularly, relates to methods for implanting occluding devices, such as stents, in a patient's body and monitoring an occlusion.

BACKGROUND

Lumens in a patient's body can change in size, shape, and/or patency, and such changes can present complications or affect associated bodily functions. For example, the walls of the vasculature, particularly arterial walls, may develop a pathological dilatation, commonly called an aneurysm. Aneurysms are observed as a ballooning-out of the wall of an artery. This is a result of the vessel wall being weakened by disease, injury, or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but an aneurysm can have serious health consequences such as a stroke if one should rupture in the brain. Additionally, a ruptured aneurysm can also result in death.

SUMMARY

At least one aspect of the disclosure provides methods for implanting an occluding device or devices (e.g., a stent or stents) in the body. The occluding device can easily conform to the shape of the tortuous vessels of the vasculature. The occluding device can direct the blood flow within a vessel away from an aneurysm. Additionally, such an occluding device can allow adequate blood flow to be provided to adjacent structures such that those structures, whether they are branch vessels or oxygen demanding tissues, are not deprived of the necessary blood flow.

In some embodiments, provided herein are stent delivery systems that include an elongate body having a distal portion, a proximal portion, and an inner surface extending from the distal portion to the proximal portion, the distal portion being configured to extend within a blood vessel of a patient; a stent expandable from a compressed configuration to an expanded configuration, the stent having a proximal region and a distal region; a stabilizing member extending into an interior of the proximal region of the stent; and one or more hook members extending distally from the stabilizing member, each hook member having a proximal section and a distal section, wherein the distal section of each hook member releasably engages the proximal region of the stent by (i) extending through one or more interstices in the stent and (ii) curving proximally toward a free end of the hook member.

Some embodiments further include a proximal retaining member concentrically disposed within the elongate body and defining a central aperture, and wherein the stabilizing member extends within the central aperture. Some embodiments further include a tubular member coupled to the proximal retaining member and extending proximally therefrom. In some embodiments, the tubular member comprises a laser cut tube having a plurality of serrations along its axial length. In certain embodiments, the proximal section of at least one of the one or more hook members extends into the central aperture and is secured thereto via a frictional engagement between the central aperture and the stabilizing member. In some embodiments, the stabilizing member comprises a hypotube.

In some embodiments, the one or more hook members comprises a shape memory material. Some embodiments provide that the distal section of at least one of the one or more hook members is configured to unfurl and disengage the stent when unrestrained by the elongate member. In some embodiments, the distal section of at least one of the one or more hook members is configured to unfurl and disengage the stent at a predetermined temperature. In certain embodiments, the proximal section of at least one of the one or more hook members is coupled to the stabilizing member.

In some embodiments, the distal section of at least one of the one or more hook members extends through the one or more interstices from an interior surface of the stent to an exterior surface of the stent. In certain embodiments, the distal section of at least one of the one or more hook members extends through the one or more interstices from an exterior surface of the stent to an interior surface of the stent.

Some methods describe deploying a stent in a vessel of a patient, and include extending an elongate body within the vessel, the elongate body having a distal portion, a proximal portion, and an inner surface extending from the distal portion to the proximal portion; advancing, relative to and within the elongate body, a stent in a compressed configuration, the stent being engaged at a proximal region by one or more hook members extending distally from the proximal retaining member, each hook member having a proximal section and a distal section, wherein the distal section of each hook member releasably engages the stent by (a) extending through one or more interstices defined by the stent and (b) curving proximally toward a free end of the hook member; expanding a distal region of the stent to an expanded configuration by advancing the distal region out of the distal portion of the elongate body; and releasing engagement of the stent by the one or more hook members by advancing the proximal region out of the distal portion of the elongate body, thereby permitting the one or more hook members to unfurl and disengage the stent.

In some methods, releasing the stent comprises unrestraining the one or more hook members from being interposed between the stent and the inner surface of the elongate body. In some methods, releasing the stent further comprises increasing a temperature of the one or more hook members to a predetermined temperature. In certain methods, the distal section of at least one of the one or more hook members extends through the one or more interstices from an interior surface of the stent to an exterior surface of the stent. In certain methods, the distal section of at least one of the one or more hook members extends through the one or more interstices from an exterior surface of the stent to an interior surface of the stent. Some methods further include withdrawing the stent back into the elongate member while one or more hook members remain releasably engaged with the proximal region of the stent.

Some embodiments described herein provide a stent delivery system that includes an elongate body having a distal portion, a proximal portion, and an inner surface extending from the distal portion to the proximal portion, the distal portion being configured to extend within a blood vessel of a patient; a stent having a proximal region and a distal region and being expandable from a compressed configuration to an expanded configuration; a proximal retaining member concentrically disposed within the elongate body; and a plurality of hook members extending distally from the proximal retaining member, each hook member having (a) a proximal section that releasably engages the stent proximal region by extending through one or more interstices defined by the stent and (b) a distal section that extends proximally and is interposed between the inner surface of the elongate body and an exterior surface of the stent while the stent is in the compressed configuration.

In some embodiments, the one or more hook members comprises a shape memory material. Some embodiments provide that at least one of the plurality of hook members is configured to unfurl and disengage the stent when the distal section is advanced out of the elongate member. In some embodiments, at least one of the plurality of hook members is configured to unfurl and disengage the stent upon reaching a predetermined temperature. In some embodiments, at least one of the plurality of hook members extends through the one or more interstices from an interior surface of the stent to an exterior surface of the stent. In certain embodiments, at least one of the one or more hook members extends through the one or more interstices from an exterior surface of the stent to an interior surface of the stent.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 2 illustrates a partial cross-sectional view of an exemplary stent delivery system, according to one or more embodiments disclosed.

FIG. 3 illustrates the stent delivery system of FIG. 2 in a partially deployed configuration, according to one or more embodiments.

FIG. 4 illustrates the stent delivery system of FIG. 2 in a fully deployed configuration, according to one or more embodiments.

FIG. 5 illustrates a partial cross-sectional view of another embodiment of the exemplary stent delivery system of FIG. 2, according to one or more embodiments.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1:
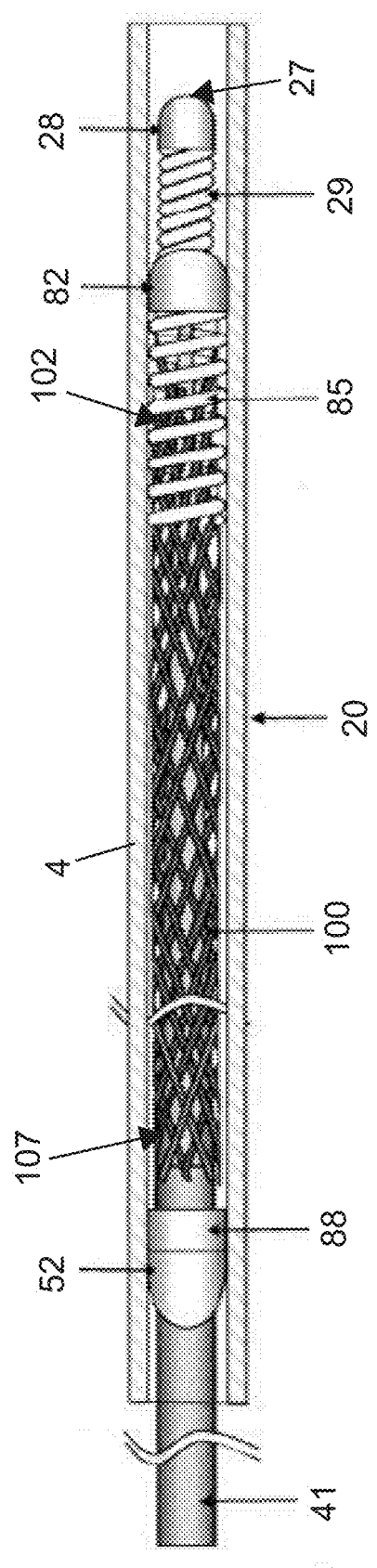
FIG. 1 is a partial cross-sectional view of an exemplary stent delivery system, according to one or more embodiments disclosed.

Described herein are various embodiments of stent delivery systems exhibiting small cross-sections which are highly flexible. Referring to FIG. 1, illustrated is an exemplary stent delivery system 20 including a stent 100 carried by a core wire 41 as arranged within an introducer sheath or catheter 4. The stent 100 and the core wire 41 may be cooperatively movable within the catheter 4 in order to deliver the stent 100 to a predetermined treatment site, such as an aneurysm, within the vasculature of a patient. Accordingly, the catheter 4 may be configured to be introduced and advanced through the vasculature of the patient. The catheter 4 may be made from various thermoplastics, e.g., PTFE, FEP, HDPE, PEEK, etc., which may optionally be lined on the inner surface of the catheter 4 or an adjacent surface with a hydrophilic material such as PVP or some other plastic coating. Additionally, either surface may be coated with various combinations of different materials, depending upon the desired results.

The stent 100 may be characterized as a vascular occluding device and/or a vascular embolization device, as generally known in the art. These terms are broad terms and are intended to have their ordinary meaning and include, unless expressly otherwise stated or incompatible with the description of, each of the stents and other vascular devices described herein. In some embodiments, the stent 100 may be a self-expanding stent made of two or more round or ovoid wire filaments. The filaments may be formed of known flexible materials including shape memory materials, such as nitinol, platinum and stainless steel. In some embodiments, the stent 100 is fabricated from platinum/8% tungsten and 35N LT (cobalt nickel alloy, which is a low titanium version of MP35N alloy) alloy wires. In other embodiments, one or more of the filaments can be formed of a biocompatible metal material or a biocompatible polymer. The stent 100 can optionally be similar to any of the versions or sizes of the PIPELINE™ Embolization Device marketed by Covidien of Mansfield, Mass. USA.

The wire filaments may be braided into a resulting lattice-like structure. In at least one embodiment, during braiding or winding of the stent 100, the filaments may be loosely braided using a 1-over-2-under-2 system. In other embodiments, however, other methods of braiding may be followed, without departing from the scope of the disclosure. The stent 100 may exhibit a porosity configured to reduce haemodynamic flow into and/or induce thrombosis within, for example, an aneurysm, but simultaneously allow perfusion to an adjacent branch vessel. As will be appreciated, the porosity of the stent 100 may be adjusted by "packing" the stent during deployment, as known in the art. The ends of the stent 100 may be cut to length and therefore remain free for radial expansion and contraction. The stent 100 may exhibit a high degree of flexibility due to the materials used, the density (i.e., the porosity) of the filaments, and the fact that the ends are not secured.

The flexibility of the core wire 41 allows the stent delivery system 20 to bend and conform to the curvature of the vasculature as needed for positional movement of the stent 100 within the vasculature. The core wire 41 may be made of a conventional guidewire material and have a solid cross-section. Alternatively, the core wire 41 can be formed from a hypotube. The material used for the core wire 41 can be any of the known guidewire materials including superelastic metals or shape memory alloys, e.g., nitinol. Alternatively, the core wire 41 can be formed of metals such as stainless steel.

In one or more embodiments, the stent delivery system 20 may exhibit the same degree of flexion along its entire length. In other embodiments, however, the stent delivery system 20 can have two or more longitudinal sections, each with differing degrees of flexion/stiffness. The different degrees of flexions for the stent delivery system 20 can be created using different materials and/or thicknesses within different longitudinal sections of the core wire 41. In another embodiment, the flexion of the core wire 41 can be controlled by spaced cuts (not shown) formed within the core wire 41. These cuts can be longitudinally and/or circumferentially spaced from each other.

A tip 28 and flexible tip coil 29 may be secured to the distal end 27 of the delivery core wire 41. The tip 28 can be characterized as a distal solder joint formed of a continuous end cap or cover as shown in the figures, which securely receives a distal end of the tip coil 29. Flexion control is provided to the distal end 27 of the delivery core wire 41 by the tip coil 29. However, in an embodiment, the tip 28 can be free of the coil 29. As illustrated, the tip 28 may have a non-percutaneous, atraumatic end face. The tip coil 29 may be configured to surround at least a portion of the core wire 41. The tip coil 29 is flexible so that it will conform to and follow the path of a vessel within the patient as the tip 28 is advanced along the vessel and the core wire 41 bends to follow the tortuous path of the vasculature.

At the proximal end 107 of the stent 100, a proximal solder joint 52 and proximal marker 88 prevent or limit lateral movement of the stent 100 along the length of the core wire 41 in the direction of the proximal end 107. As illustrated, the proximal end 107 of the stent 100 may be axially-offset from the proximal marker 88 by a short distance. In other embodiments, however, the stent 100 may shift axially during introduction into the vasculature of the patient and contact the proximal marker 88 which prevents or limits the stent 100 from moving along the length of the core wire 41 away from a distally-located protective coil 85 coupled to an adjacent or mid solder joint 82.

After navigating the length of the catheter 4 to the predetermined treatment site within the patient, the stent 100 may be deployed from the catheter 4 in a variety of ways. In one embodiment, the catheter 4 is retracted while maintaining the position of the core wire 41 to expose the distal end 27 of the of the delivery core wire 41 and the distal end 102 of the stent 100. Upon exiting the catheter 4, the portion of the stent 100 that is not situated between the protective coil 85 and the core wire 41 and that is not covered by the catheter 4 begins to expand radially. The catheter 4 may then be further retracted until enough of the stent 100 is exposed such that the expansion diameter of the stent 100 is sufficient to engage the walls of the vessel (not shown), such as a blood vessel. Upon engaging a portion of said vessel, the stent 100 may be at least partially anchored within the vessel.

The core wire 41 may then be rotated at its proximal end, which causes rotation at the distal end 27 relative to the stent 100. The rotation of the core wire 41 also causes twisting of the protective coil 85, which pushes the distal end 102 of the stent 100 out from beneath the protective coil 85 like a corkscrew. Once the distal end 102 of the stent 100 is released from the protective coil 85, it expands to engage the walls of the vessel. The catheter 4 may then be further retracted to expose and expand the remaining portions of the stent 100.

Those skilled in the art will readily recognize that variations of this deployment method are possible. For example, the catheter 4 may be further retracted before rotating the core wire 41, such as by expanding the proximal end 107 of the stent 100 before expanding the distal end 102. Other examples of deployment variations include causing or otherwise creating variable porosity of the stent 100.

Once the entire stent 100 is expanded, the core wire 41 may then be retracted back into the catheter 4 by pulling proximally on the core wire 41 and maintaining the catheter 4 in its position. The proximal taper of the solder joint 52 coupled to the proximal marker 88 helps guide retraction of the core wire 41 back into the catheter 4. The core wire 41 and the catheter 4 may then be both retracted from the vessel and vasculature of the patient.

Referring now to FIG. 2, illustrated is a cross-sectional view of another exemplary stent delivery system 5, according to one or more embodiments disclosed. The system 5 may include an elongate body, such as a catheter 8, a core wire assembly 57 extending generally longitudinally through the catheter 8, and a stent 66 loaded onto the core wire assembly 57. The core wire assembly 57 may be slidably received within the catheter 8 and used to deploy the stent 66 in a lumen, such as the blood vessel 69 shown in FIGS. 4-7 below.

In some embodiments, the stent 66 may be a self-expanding stent that includes a tubular lattice structure movable between a compressed configuration and an expanded configuration. The stent 66 includes an interior surface 40a, an exterior surface 40b, a distal end 67, and a proximal end 68. The stent 66 may be loaded onto the core wire assembly 57 in a compressed configuration within the catheter 8, as shown in FIG. 2. In one or more embodiments, the stent 66 is maintained in its compressed configuration within the catheter 8 by an inner surface 17 of the catheter 8. The stent 66 may be configured to automatically expand radially from its compressed configuration to its expanded configuration as the stent 66 is deployed from the catheter 8 and into a blood vessel, as discussed in more detail below.

The elongate body or catheter 8 has a proximal portion 18a and a distal portion 18b. At the distal portion 18b, the catheter 8 defines a distal opening 19 through which the core wire assembly 57 may be advanced beyond the distal portion 18b in order to deploy the stent 66 within the blood vessel. A proximal opening (not shown) is defined at the opposing end of the catheter 8 through which the core wire assembly 57 is initially inserted into the catheter 8.

Referring now to FIG. 2, illustrated is a partial cross-sectional view of an exemplary stent delivery system 5, according to one or more embodiments disclosed. The system 5 may include an elongate body 8 having a stent 66 concentrically disposed therein for delivery to a treatment site. The elongate body 8 may be any type of delivery device or tubular, such as a catheter or a delivery sheath, as known in the art. In one embodiment, the elongate body 8 may be substantially similar to the catheter 4 described above with reference to FIG. 1. The elongate body 8 has a proximal portion 18a and a distal portion 18b. At the distal portion 18b, the elongate body 8 defines a distal opening 19 through which the stent 66 may be advanced beyond the distal portion 18b in order to be deployed at the treatment site, for example, within a patient's vasculature. As with the catheter 4 described above, the elongate body 8 may be made from any suitable material such as, but not limited to, a thermoplastic elastomer, urethane, polymer, polypropylene, plastic, ethelene chlorotrifluoroethylene (ECTFE), polytetrafluoroethylene (PTFE), fluorinated ethylene propylene copolymer (FEP), nylon, PEBAX® block copolymer, VESTAMID® plastic resin, TECOFLEX® thermoplastic polyurethanes, HALAR® fluoropolymer, HYFLON® fluoropolymers, PELLETHANE® polyurethane, combinations thereof, and the like.

The stent 66 may substantially similar to the stent 100 described above with reference to FIG. 1. As illustrated, the stent 66 includes an interior surface 40a, an exterior surface 40b, a distal end 67, and a proximal end 68. The stent 66 may be a self-expanding stent that includes a tubular lattice structure movable between a compressed configuration and an expanded configuration. As depicted in FIG. 2, the stent 66 is arranged within the elongate body 8 in its compressed configuration, where the exterior surface 40b biases against an inner surface 17 of the elongate body 8. When unrestrained by the elongate body 8, the stent 66 may be configured to automatically expand to its expanded configuration.

The system 5 may further include a delivery guidewire 57, a proximal retaining member 26, and a delivery tubular member 60, each also concentrically disposed within the elongate body 8. The delivery guidewire 57 has a proximal end 53a and a distal end 53b. The proximal retaining member 26 and the delivery tubular member 60 may be slidably received within the elongate body 8 and arranged about the delivery guidewire 57 in order to deliver the stent 66 to the treatment site. In operation, the proximal retaining member 26, the delivery tubular member 60, and the elongate member 8 may be cooperatively used to help deploy the stent 66 into the patient's vasculature. In some embodiments, the proximal retaining member 26 may operate as a pusher device configured to advance the stent 66 through the elongate member 8. In some embodiments, advancement of the stent 66 through the elongate member 8 may be assisted by bumpers (not shown), or enlarged portions positioned on the guidewire 57 that frictionally engage the stent 66 while the stent 66 is within the elongate member 8.

In at least one embodiment, the proximal retaining member 26 is made of PEEK tubing. In other embodiments, however, the proximal retaining member 26 may be made of platinum or another material or substance visible through CAT scan, X-Ray, MRI, or ultrasound technology. Accordingly, a user may be able to pinpoint the location and track the progress of the stent 66 within the elongate body 8 or blood vessel by determining the location of the proximal retaining member 26. The proximal retaining member 26, in some embodiments, can be configured and act as a pusher to contact and advance the stent 66 out of the elongate body 8.

In one or more embodiments, the delivery tubular member 60 may be coupled or otherwise attached to the proximal retaining member 26 and extend proximally therefrom. In other embodiments, however, the delivery tubular member 60 may be integrally formed with the proximal retaining member 26. In some embodiments, the delivery tubular member 60 may be a laser cut tube defining a plurality of grooves or serrations 59 along its axial length. The serrations 59 may provide an amount of flexure to the delivery tubular member 60 in order to be able to manipulate the tortuous vasculature of the patient.

The system 5 may further include a stabilizing member 62 arranged about the delivery guidewire 57. In one or more embodiments, the stabilizing member 62 may be received into a central aperture 61 defined in the proximal retaining member 26. Accordingly, the stabilizing member 62 may be translatable within the elongate member 8 along with the proximal retaining member 26. As illustrated, the stabilizing member 62 may extend a short distance into the interior of the stent 66 in order to provide an added amount of rigidity to the stent 66 during translation within the elongate member 8. In one or more embodiments, the stabilizing member 62 may be a hypotube, or may be any other type of tubular device. Moreover, the stabilizing member 62 may be made from materials similar to the material(s) that comprise the elongate member 8.

The system 5 may further include one or more hook members 58 configured to releasably engage the stent 66. Each of the hook members 58 may have a proximal section 54a and a distal section 54b, each section 54a,b being able to curve and/or bend. Although only two elongate hook members 58 are depicted in FIG. 2, it will be appreciated that any number of hook members 58 may be employed without departing from the scope of the disclosure. The hook members 58 may be made of a wide variety of metallic or polymeric materials, and/or combinations thereof. In at least one embodiment, however, the hook members 58 are made of shape memory material, such as nitinol. In other embodiments, the hook members 58 are made from elastic materials, super-elastic materials, or the like.

In at least one embodiment, the proximal section 54a of each hook member 58 may be coupled or otherwise secured to the stabilizing member 62. For example, the proximal ends 54a may also extend into the central aperture 61 and be secured thereto via a frictional biasing engagement between the central aperture 61 and the stabilizing member 62. In other embodiments, however, the proximal section 54a of each elongate hook member 58 may be coupled or otherwise attached directly to the stabilizing member 62 and/or the retaining member 26. In yet other embodiments, the stabilizing member 62 may be entirely omitted, and the proximal section 54a of each elongate hook member 58 may be coupled or otherwise attached directly to the proximal retaining member 26.

The hook members 58 may be configured to releasably engage the stent 66 at or near the proximal end 68 of the stent 66. As illustrated, the distal section 54b of each hook member 58 may extend through one or more of the interstices defined by the braided stent 66, from the interior surface 40a to the exterior surface 40b, and "hook" or otherwise curve back proximally. During operation, the distal section 54b of each hook member 58 may be maintained in the curved or hooked position as a result of being interposed between the exterior surface 40b of the stent 66 and the inner surface 17 of the elongate body 8. In other words, the expansive force exhibited by the stent 66 as it is restrained in its compressed configuration helps maintain the distal ends 54h between the inner surface 17 of the elongate member 8 and the exterior surface 40b of the stent 66.

A distal cap 71 may be arranged about the delivery guidewire 57 distal the elongate member 8. The distal cap 71 may serve to help maintain the stent 66 in its compressed configuration until the stent 66 is to be deployed at the treatment site. In one or more embodiments, the distal cap 71 may be substantially similar to the distal solder joint 28 as described above with reference to FIG. 1. Moreover, the distal cap 71 may be configured with an atraumatic end face, such as a rounded or smoothed face. In other embodiments, the distal cap 71 can have other atraumatic shapes designed to prevent injury to the vessel into which it may be introduced. In at least one embodiment, the distal cap 71 may be made from CHRONOPRENE™. In other embodiments, the distal cap 71 may be made from other materials such as, but not limited to, thermoplastics, rubbers, elastomers, combinations thereof, and the like. In some embodiment, the distal cap 71 can define a cavity to permit a distal portion of the stent 66 to be placed therein, such that the distal cap 71 can operate similar to the protective coil 85, as described in FIG. 1 above. Additionally, in some embodiments, the distal cap 71 can be replaced with a protective coil 85 (FIG. 1).

Referring to FIG. 3, illustrated is the stent delivery system 5 where the stent 66 is moved into a partially deployed configuration, according to one or more embodiments. In exemplary operation of the stent delivery system 5, the elongate body 8 is percutaneously introduced into a blood vessel 69 and advanced to a treatment site therein, such as at or near the neck of an aneurysm (not shown). In one embodiment, the elongate body 8 is guided to the treatment site using fluoroscopic imaging, in which one or more radio-opaque markers (not shown) are placed on the distal portion 18b of the elongate body 8 to indicate a position of the elongate body 8 in a fluoroscopic image. The elongate body 8 may also be guided using other imaging techniques including, but not limited to, ultrasound and magnetic resonance imaging.

Once the elongate body 8 is positioned at or near the treatment site, the stent 66 may be deployed into the blood vessel 69 by retracting the elongate body 8 proximally relative to the stent 66. As the elongate body 8 is retracted, the proximal retaining member 26 biases the proximal end 68 of the stent 66, thereby precluding its proximal translation and forcing the distal end 67 of the stent 66 to advance beyond the distal portion 18b of the elongate body 8. Once the distal end 67 exits the distal opening 19 it automatically expands to its natural, expanded configuration. In its expanded configuration, the exterior surface 40b of the stent 66 may extend to and contact the inner surface 55 of the blood vessel 69.

Before the stent 66 is fully deployed into the blood vessel 69, however, the stent 66 may be retracted or otherwise resheathed back into the elongate body 8 using the one or more hook members 58. For example, as long as the hook members 58 remain extended through one or more of the interstices defined in the stent 66, the stent 66 may be resheathed by moving the delivery tubular member 60 and proximal retaining member 26 proximally with respect to the elongate member 8. Since the hook members 58 are coupled to the proximal retaining member 26 or the stabilizing member 62, proximal movement of the proximal retaining member 26 will correspondingly move the hook members 58, and the stent 66 conveniently hooked thereto, proximally.

In embodiments where the proximal end 68 of the stent 66 is not welded, braided, or otherwise closed, multiple hook members 58 may be required to effectively retract the stent 66 proximally without damaging the stent 66 or prematurely disengaging the hook members 58 from the stent 66. Using multiple hook member 58 may serve to spread out retrieval forces over a larger area. Accordingly, multiple hook members 58 may be spaced about the circumference of the stent 66 to enable effective resheathing of the stent 66. In one embodiment, the multiple hook members 58 may be equidistantly spaced about the circumference of the stent 66 to effectively spread out the retrieval forces. In other embodiments, however, the multiple hook members 58 may be randomly spaced about the circumference of the stent 66, without departing from the scope of the disclosure.

As can be appreciated, this may prove beneficial when the initial deployment site of the stent 66 is incorrect or the stent 66 otherwise has to be relocated to properly cover the treatment site. Accordingly, the stent 66 can be partially deployed, resheathed, and relocated multiple times in order to ensure that the stent 66 is properly deployed in the correct location for best use. Moreover, this feature may prove advantageous and intuitive for users (e.g., physicians), since the stent 66 may be delivered by pushing the delivery tube 60 distally and resheathed by pulling the delivery tube 60 proximally.

Referring to FIG. 4, the stent 66 may be fully deployed by advancing the proximal end 68 of the stent 66 past the distal end 18b of the elongate member 8. Unrestrained by the elongate member 8, the proximal end 68 will expand to its expanded configuration and the hook members 58 may be configured to correspondingly unfurl and/or be withdrawn proximally or radially inward from engagement with the stent 66. In at least one embodiment, the distal section 54b of each hook member 58 may straighten once not being restrained by the elongate member 8. In other embodiments, however, the distal section 54b of each hook member 58 may straighten upon being exposed to elevated temperatures or other external stimuli found within the patient's vasculature.

The delivery system 5 of FIGS. 2-3 can be employed in a method of deploying the stent 66/100 as follows. First, the distal portion of the delivery system is advanced within a blood vessel to the treatment location which in this example is (but need not be) at or near the neck of an aneurysm formed in the blood vessel. The delivery system 5 is then operated to partially deploy the stent 66/100, using any suitable method disclosed herein, such that the distal end of the stent is expanded and in contact with the blood vessel wall at a location distal of the aneurysm neck. This partial deployment step may optionally further include deploying a further portion (e.g., a midsection) of the stent into the vessel such that it extends across part of or the entire aneurysm neck, using any suitable method disclosed herein. Following initial partial deployment, one or all of the hook members 58 can remain engaged with the stent 66/100 to facilitate re-sheathing the stent if desired. At this point the user may optionally inspect the partial deployment of the stent and, if the partial deployment is not satisfactory, re-sheath the stent either completely or partially, and attempt to re-deploy the re-sheathed portion(s) of the stent, e.g. as described elsewhere herein. If the partial deployment is satisfactory, or if the user declines to inspect the position of the stent following partial deployment, the remaining undeployed portion of the stent may be deployed, e.g. using any of the various techniques disclosed herein, so as to position the proximal end 68 of the stent 66 in the blood vessel at a location proximal of the aneurysm neck. The stent 66/100 is therefore now positioned in the blood vessel and extends across the aneurysm neck, with its distal end 67 distal of the neck, and its proximal end 68 proximal of the neck. With the stent thus deployed, it can treat the aneurysm by impeding blood flow into the aneurysm to a degree sufficient to induce thrombosis inside (and lead to elimination of) the aneurysm. This method of deploying the stent 66/100, or any combination of the steps thereof, may be performed with any suitable apparatus including any of the various embodiments of the delivery system 5 disclosed herein, or other apparatus, and/or in combination with any other methods disclosed herein (or any steps thereof), or other methods.

Referring to FIG. 5, illustrated is a partial cross-sectional view of another embodiment of the stent delivery system 5, according to one or more embodiments disclosed. Similar to the embodiment shown in FIG. 2, the one or more hook members 58 may be configured to releasably engage the stent 66 at or near the proximal end 68 of the stent 66. As illustrated in FIG. 5, however, the distal section 54b of each hook member 58 may be adapted to extend through one or more of the interstices defined in the stent 66 from the exterior surface 40b to the interior surface 40a. The distal section(s) 54b may curve back proximally in order to capture or "hook" the stent 66 for resheathability. It is further contemplated herein to have a combination of one or more hook members 58 extending through the interstices from the exterior surface 40b to the interior surface 40a and one or more other hook members 58 extending through the interstices 34 from the interior surface 40a to the exterior surface 40b, without departing from the scope of the disclosure.

Each hook member 58 may be maintained in releasable engagement with the stent 66 as a result of being interposed between the exterior surface 40b of the stent 66 and the inner surface 17 of the elongate body 8. Once the stent 66 becomes unrestrained by the elongate member 8, however, the proximal end 68 will expand to its expanded configuration and the hook members 58 will correspondingly unfurl from engagement with the stent 66. As with prior embodiments, the distal section 54b of each hook member 58 may straighten once not being restrained by the elongate member 8, but also may straighten upon being exposed to elevated temperatures or other external stimuli found within the patient's vasculature.

Figure 6:
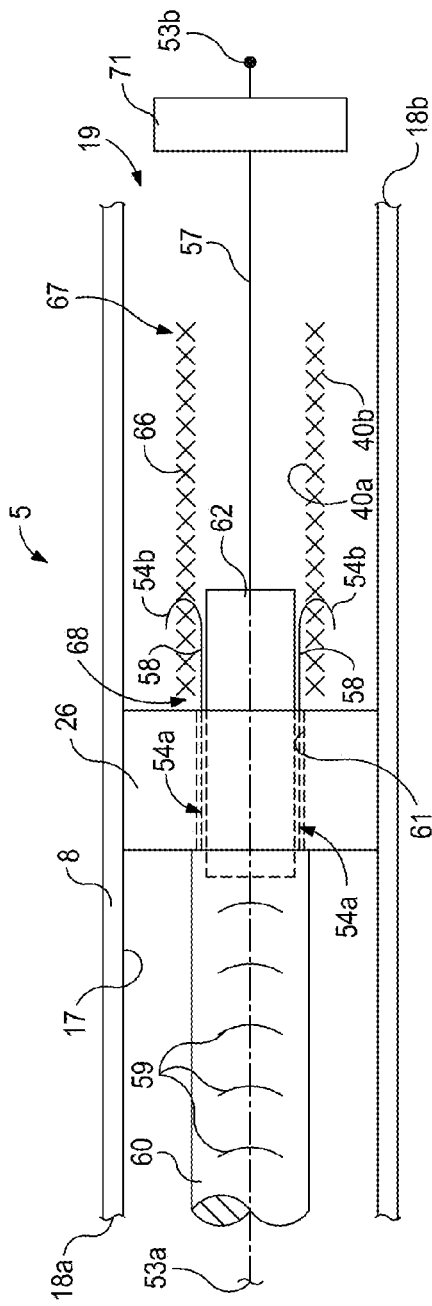
FIG. 6 illustrates a partial cross-sectional view of another embodiment of the exemplary stent delivery system of FIG. 2, according to one or more embodiments.

Referring now to FIG. 6, illustrated is a partial cross-sectional view of another embodiment of the stent delivery system 5, according to one or more embodiments disclosed. As illustrated, the stent 66 is in a compressed configuration substantially adjacent the outside surface of the stabilizing member 62. In the illustrated embodiment, the stent 66 may be configured to expand to its expanded configuration once coming into contact with an external stimulus, such as a thermal or chemical activator. For example, as the stent 66 is deployed from the elongate body 8 and into the patient's vasculature, the heat emanating from the patient may thermally activate the stent 66 such that it is caused to expand. In other embodiments, the stent 66 may be configured to react with chemicals either found naturally in a patient's vasculature or through strategic injection by the user. As a result, the one or more hook members 58 may maintain the "hooked" engagement with the stent 66 until the stent 66 reacts and is deployed into its expanded configuration.

The one or more hook members 58 may releasably engage the stent 66 at or near the proximal end 68 of the stent 66. As illustrated, the distal section 54b of each hook member 58 may extend through the interstices defined in the stent 66, from the interior surface 40a to the exterior surface 40b, and "hook" or otherwise curve back proximally. Similar to the embodiment shown in FIG. 5, however, the hook members 85 could equally extend through the stent 66 from the exterior surface 40b to the interior surface 40a, or combinations thereof, without departing from the scope of the disclosure. The hook members 58 may be made of shape memory materials, such as nitinol, and configured to remain in the curved position until acted upon by an external stimulus (e.g., temperature, chemicals, etc.). Similar to the stent 66, in at least one embodiment the hook members 58 may be configured to straighten out, unfurl, or otherwise disengage the stent 66 once reaching the temperature of the patient's vasculature.

Figure 7:
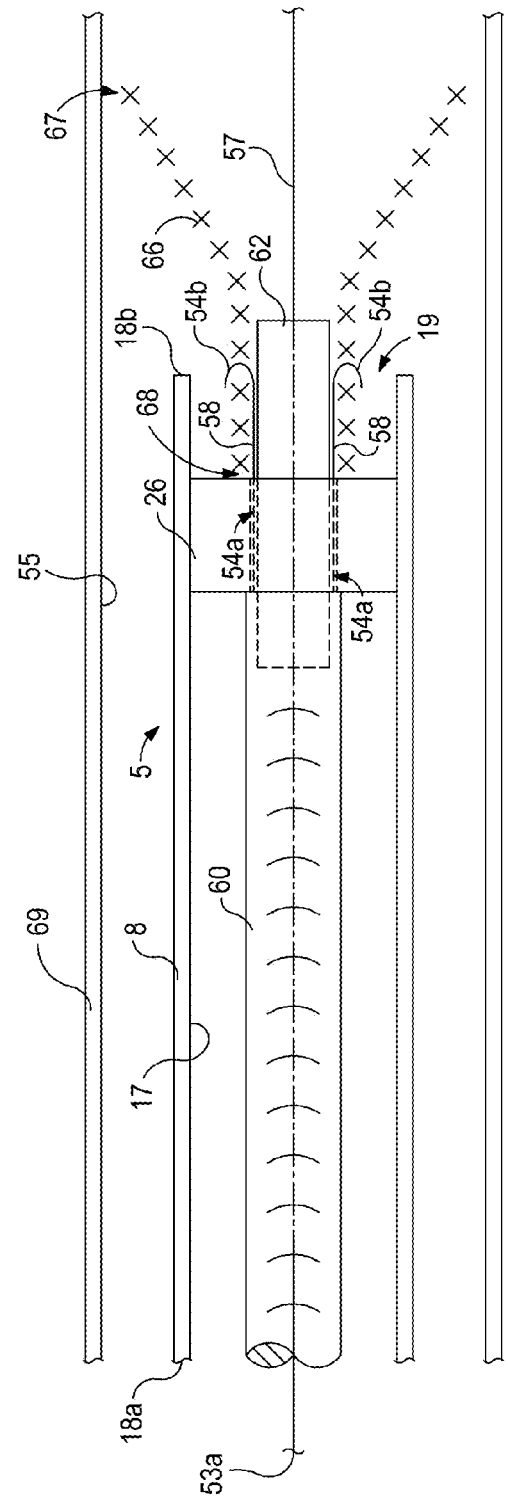
FIG. 7 illustrates the stent delivery system of FIG. 6 in a partially deployed configuration, according to one or more embodiments.

FIG. 7 illustrates the stent delivery system 5 of FIG. 6 where the stent 66 has moved into a partially deployed configuration, according to one or more embodiments. The stent 66 may be deployed into the blood vessel 69 by retracting the elongate body 8 proximally relative to the stent 66. As the elongate body 8 is retracted, the distal end 67 of the stent 66 may advance beyond the distal portion 18b of the elongate body 8 and begin to expand once reacting with the external stimulus (e.g., temperature, chemicals, etc.). Before the stent 66 is fully deployed into the blood vessel 69, however, and before the hook members 58 straighten out, unfurl, or otherwise disengage the stent 66, the stent 66 may be able to be retracted or otherwise resheathed back into the elongate body 8 using the hook members 58. As long as the hook members 58 remain extended through one or more of the interstices of the stent 66 and curved or "hooked" proximally, the stent 66 may be resheathed by moving the delivery tubular member 60 and proximal retaining member 26 proximally with respect to the elongate member 8. Since the hook members 58 are coupled to the proximal retaining member 26 and/or the stabilizing member 62, proximal movement of the proximal retaining member 26 will correspondingly move the hook members 58, and the stent 66 conveniently hooked thereto, proximally.

The apparatus and methods discussed herein are not limited to the deployment and use of an occluding device within any particular vessels, but may include any number of different types of vessels. For example, in some aspects, vessels may include arteries or veins. In some aspects, the vessels may be suprathoracic vessels (e.g., vessels in the neck or above), intrathoracic vessels (e.g., vessels in the thorax), subthoracic vessels (e.g., vessels in the abdominal area or below), lateral thoracic vessels (e.g., vessels to the sides of the thorax such as vessels in the shoulder area and beyond), or other types of vessels and/or branches thereof.

In some aspects, the stent delivery systems disclosed herein may be deployed within superthoracic vessels. The suprathoracic vessels may comprise at least one of intracranial vessels, cerebral arteries, and/or any branches thereof. For example, the suprathoracic vessels may comprise at least one of a common carotid artery, an internal carotid artery, an external carotid artery, a middle meningeal artery, superficial temporal arteries, an occipital artery, a lacrimal (ophthalmic) artery, an accessory meningeal artery, an anterior ethmoidal artery, a posterior ethmoidal artery, a maxillary artery, a posterior auricular artery, an ascending pharyngeal artery, a vertebral artery, a left middle meningeal artery, a posterior cerebral artery, a superior cerebellar artery, a basilar artery, a left internal acoustic (labyrinthine) artery, an anterior inferior cerebellar artery, a left ascending pharyngeal artery, a posterior inferior cerebellar artery, a deep cervical artery, a highest intercostal artery, a costocervical trunk, a subclavian artery, a middle cerebral artery, an anterior cerebral artery, an anterior communicating artery, an ophthalmic artery, a posterior communicating artery, a facial artery, a lingual artery, a superior laryngeal artery, a superior thyroid artery, an ascending cervical artery, an inferior thyroid artery, a thyrocervical trunk, an internal thoracic artery, and/or any branches thereof. The suprathoracic vessels may also comprise at least one of a medial orbitofrontal artery, a recurrent artery (of Heubner), medial and lateral lenticulostriate arteries, a lateral orbitofrontal artery, an ascending frontal (candelabra) artery, an anterior choroidal artery, pontine arteries, an internal acoustic (labyrinthine) artery, an anterior spinal artery, a posterior spinal artery, a posterior medial choroidal artery, a posterior lateral choroidal artery, and/or branches thereof. The suprathoracic vessels may also comprise at least one of perforating arteries, a hypothalamic artery, lenticulostriate arteries, a superior hypophyseal artery, an inferior hypophyseal artery, an anterior thalamostriate artery, a posterior thalamostriate artery, and/or branches thereof. The suprathoracic vessels may also comprise at least one of a precentral (pre-Rolandic) and central (Rolandic) arteries, anterior and posterior parietal arteries, an angular artery, temporal arteries (anterior, middle and posterior), a paracentral artery, a pericallosal artery, a callosomarginal artery, a frontopolar artery, a precuneal artery, a parietooccipital artery, a calcarine artery, an inferior vermian artery, and/or branches thereof.

In some aspects, the suprathoracic vessels may also comprise at least one of diploic veins, an emissary vein, a cerebral vein, a middle meningeal vein, superficial temporal veins, a frontal diploic vein, an anterior temporal diploic vein, a parietal emissary vein, a posterior temporal diploic vein, an occipital emissary vein, an occipital diploic vein, a mastoid emissary vein, a superior cerebral vein, efferent hypophyseal veins, infundibulum (pituitary stalk) and long hypophyseal portal veins, and/or branches thereof.

The intrathoracic vessels may comprise the aorta or branches thereof. For example, the intrathoracic vessels may comprise at least one of an ascending aorta, a descending aorta, an arch of the aorta, and/or branches thereof. The descending aorta may comprise at least one of a thoracic aorta, an abdominal aorta, and/or any branches thereof. The intrathoracic vessels may also comprise at least one of a subclavian artery, an internal thoracic artery, a pericardiacophrenic artery, a right pulmonary artery, a right coronary artery, a brachiocephalic trunk, a pulmonary trunk, a left pulmonary artery, an anterior interventricular artery, and/or branches thereof. The intrathoracic vessels may also comprise at least one of an inferior thyroid artery, a thyrocervical trunk, a vertebral artery, a right bronchial artery, a superior left bronchial artery, an inferior left bronchial artery, aortic esophageal arteries, and/or branches thereof.

In some aspects, the intrathoracic vessels may also comprise at least one of a right internal jugular vein, a right brachiocephalic vein, a subclavian vein, an internal thoracic vein, a pericardiacophrenic vein, a superior vena cava, a right superior pulmonary vein, a left brachiocephalic vein, a left internal jugular vein, a left superior pulmonary vein, an inferior thyroid vein, an external jugular vein, a vertebral vein, a right highest intercostal vein, a 6th right intercostal vein, an azygos vein, an inferior vena cava, a left highest intercostal vein, an accessory hemiazygos vein, a hemiazygos vein, and/or branches thereof.

In some aspects, the subthoracic vessels may comprise at least one of renal arteries, inferior phrenic arteries, a celiac trunk with common hepatic, left gastric and splenic arteries, superior suprarenal arteries, a middle suprarenal artery, an inferior suprarenal artery, a right renal artery, a subcostal artery, 1st to 4th right lumbar arteries, common iliac arteries, an iliolumbar artery, an internal iliac artery, lateral sacral arteries, an external iliac artery, a testicular (ovarian) artery, an ascending branch of deep circumflex iliac artery, a superficial circumflex iliac artery, an inferior epigastric artery, a superficial epigastric artery, a femoral artery, a ductus deferens and testicular artery, a superficial external pudendal artery, a deep external pudendal artery, and/or branches thereof. The subthoracic vessels may also comprise at least one of a superior mesenteric artery, a left renal artery, an abdominal aorta, an inferior mesenteric artery, colic arteries, sigmoid arteries, a superior rectal artery, 5th lumbar arteries, a middle sacral artery, a superior gluteal artery, umbilical and superior vesical arteries, an obturator artery, an inferior vesical and artery to ductus deferens, a middle rectal artery, an internal pudendal artery, an inferior gluteal artery, a cremasteric, pubic (obturator anastomotic) branches of inferior epigastric artery, a left colic artery, rectal arteries, and/or branches thereof.

In some aspects, the lateral thoracic vessels may comprise at least one of humeral arteries, a transverse cervical artery, a suprascapular artery, a dorsal scapular artery, and/or branches thereof. The lateral thoracic vessels may also comprise at least one of an anterior circumflex humeral artery, a posterior circumflex humeral artery, a subscapular artery, a circumflex scapular artery, a brachial artery, a thoracodorsal artery, a lateral thoracic artery, an inferior thyroid artery, a thyrocervical trunk, a subclavian artery, a superior thoracic artery, a thoracoacromial artery, and/or branches thereof.

In some embodiments, a catheter, such as that described in U.S. patent application Ser. No. 12/731,110, which was filed on Mar. 24, 2010 and which incorporated herein by reference in its entirety, can be used to deliver an occluding device delivery system. The delivery system can include an expandable occluding device (e.g., stent) configured to be placed across an aneurysm that is delivered through the distal portion of the catheter, out a distal tip, and into the vasculature adjacent an aneurysm in, for example, the middle cerebral artery. A proximal portion of the catheter can remain partially or entirely within a guiding catheter during delivery, and an intermediate portion, taper portion, and distal portion of the catheter can extend distally of the guiding catheter. The occluding device can be released at the target location and can be used to occlude blood flow into the aneurysm. The catheter can be used to reach target locations (e.g., aneurysms) located elsewhere in the body as well, include but not limited to other arteries, branches, and blood vessels such as those described above.

In some embodiments, a method of implantation and monitoring can be used, for example, with the deployment systems described above. The method can include implanting an occluding device within the vasculature of a patient such that the device extends, within and along a vessel, past an aneurysm. Example occluding devices, deployment devices, microcatheters for delivery of occluding devices, and deployment methods are described in U.S. Provisional Application No. 60/574,429, filed on May 25, 2004; U.S. patent application Ser. No. 11/136,395 (U.S. Patent Application Publication No. 2005/0267568), filed on May 25, 2005; U.S. patent application Ser. No. 11/420,025 (U.S. Patent Application Publication No. 2006/0206200), filed on May 24, 2006; U.S. patent application Ser. No. 11/420,027 (U.S. Patent Application Publication No. 2006/0206201), filed on May 24, 2006; U.S. patent application Ser. No. 11/136,398 (U.S. Patent Application Publication No. 2006/0271149), filed on May 25, 2005; U.S. patent application Ser. No. 11/420,023 (U.S. Patent Application Publication No. 2006/0271153), filed on May 24, 2006; U.S. patent application Ser. No. 12/490,285 (U.S. Patent Application Publication No. 2009/0318947), filed on Jun. 23, 2010; U.S. patent application Ser. No. 12/425,604 (U.S. Patent Publication No. 2009/0287288), filed on Apr. 17, 2009; U.S. patent application Ser. No. 12/425,617 (U.S. Patent Application Publication No. 2009/0287241), filed on Apr. 17, 2009; U.S. patent application Ser. No. 12/431,716 (U.S. Patent Application Publication No. 2009/0270974), filed on Apr. 28, 2009; U.S. patent application Ser. No. 12/431,717, filed on Apr. 28, 2009; U.S. patent application Ser. No. 12/431,721 (U.S. Patent Publication No. 2009/0292348), filed on Apr. 28, 2009; U.S. patent application Ser. No. 12/490,285 (U.S. Patent Application Publication No. 2010/0010624), filed on Jun. 23, 2009; U.S. patent application Ser. No. 12/490,285 (U.S. Patent Publication No. 2009/0319017), filed on Jun. 23, 2009; U.S. patent application Ser. No. 12/731,110, filed on Mar. 24, 2010; and U.S. patent application Ser. No. 12/751,997, filed on Mar. 31, 2010; each of which is incorporated herein by reference in its entirety. Other occluding devices, deployment devices, catheters, and deployment methods are also possible.

The apparatus and methods discussed herein are not limited to the deployment and use of an occluding device or stent within the vascular system but may include any number of further treatment applications. Other treatment sites may include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component or method step is intended to be dedicated to the public regardless of whether the element, component or method step is explicitly recited in the claims.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art may be made in the arrangement, operation and details of the method and apparatus of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A stent delivery system comprising:
   an elongate body having a distal portion, a proximal portion, and an inner surface extending from the distal portion to the proximal portion, the distal portion being configured to extend within a blood vessel of a patient;
   a stent expandable from a compressed configuration to an expanded configuration, the stent having a proximal region and a distal region;
   a stabilizing member extending into an interior of the proximal region of the stent; and
   one or more hook members extending distally from the stabilizing member, each hook member having a proximal section and a distal section, each hook member having a more curved configuration wherein the distal section of each hook member releasably engages the proximal region of the stent radially between the proximal section and the distal section by (i) extending through one or more interstices in the stent and (ii) curving proximally toward a free end of the hook member, and each hook member having a less curved configuration wherein the distal section of each hook member extends distally beyond the corresponding proximal section, each hook member being biased to the less curved configuration when unrestrained, wherein the distal section of each hook member, while in the more curved configuration, engages the inner surface of the elongate body and is held radially between the stent and the inner surface of the elongate body.

2. The system of claim 1, further comprising a proximal retaining member concentrically disposed within the elongate body and defining a central aperture, and wherein the stabilizing member extends within the central aperture.

3. The system of claim 2, further comprising a tubular member coupled to the proximal retaining member and extending proximally therefrom.

4. The system of claim 3, wherein the tubular member comprises a laser cut tube having a plurality of serrations along its axial length.

5. The system of claim 2, wherein the proximal section of at least one of the one or more hook members extends into the central aperture and is secured thereto via a frictional engagement between the central aperture and the stabilizing member.

6. The system of claim 1, wherein the stabilizing member comprises a hypotube.

7. The system of claim 1, wherein the one or more hook members comprises a shape memory material.

8. The system of claim 7, wherein the distal section of at least one of the one or more hook members is configured to unfurl and disengage the stent when unrestrained by the elongate member.

9. The system of claim 7, wherein the distal section of at least one of the one or more hook members is configured to unfurl and disengage the stent at a predetermined temperature.

10. The system of claim 1, wherein the proximal section of at least one of the one or more hook members is coupled to the stabilizing member.

11. The system of claim 1, wherein the distal section of at least one of the one or more hook members extends through the one or more interstices from an interior surface of the stent to an exterior surface of the stent.

12. The system of claim 1, wherein the distal section of at least one of the one or more hook members extends through the one or more interstices from an exterior surface of the stent to an interior surface of the stent.

13. A method of deploying a stent in a vessel of a patient, comprising:
   extending an elongate body within the vessel, the elongate body having a distal portion, a proximal portion, and an inner surface extending from the distal portion to the proximal portion;
   advancing, relative to and within the elongate body, a stent in a compressed configuration, the stent being engaged at a proximal region by one or more hook members extending distally from a proximal retaining member, each hook member having a proximal section and a distal section, wherein the distal section of each hook member releasably engages the stent by (a) extending through one or more interstices defined by the stent and (b) curving proximally toward a free end of the hook member, wherein the distal section of each hook member engages the inner surface of the elongate body and is held radially between the stent and the inner surface of the elongate body;
   expanding a distal region of the stent to an expanded configuration by advancing the distal region out of the distal portion of the elongate body; and
   releasing engagement of the stent by the one or more hook members by advancing the proximal region and the distal section of each hook member out of the distal portion of the elongate body, thereby permitting the one or more hook members to unfurl and disengage the stent.

14. The method of claim 13, wherein releasing the stent comprises unrestraining the one or more hook members from being interposed between the stent and the inner surface of the elongate body.

15. The method of claim 13, wherein releasing the stent further comprises increasing a temperature of the one or more hook members to a predetermined temperature.

16. The method of claim 13, wherein the distal section of at least one of the one or more hook members extends through the one or more interstices from an interior surface of the stent to an exterior surface of the stent.

17. The method of claim 13, wherein the distal section of at least one of the one or more hook members extends through the one or more interstices from an exterior surface of the stent to an interior surface of the stent.

18. The method of claim 13, further comprising withdrawing the stent back into the elongate member while one or more hook members remain releasably engaged with the proximal region of the stent.

19. The method of claim 18, further comprising positioning the stent in the blood vessel such that it extends at least partially across the neck of an aneurysm formed in the blood vessel.

20. A stent delivery system comprising:
 an elongate body having a distal portion, a proximal portion, and an inner surface extending from the distal portion to the proximal portion, the distal portion being configured to extend within a blood vessel of a patient;
 a stent having a proximal region and a distal region and being expandable from a compressed configuration to an expanded configuration;
 a proximal retaining member concentrically disposed within the elongate body; and
 a plurality of hook members extending distally from the proximal retaining member, each hook member having (i) a restrained configuration in which (a) a proximal section releasably engages the stent proximal region by extending through one or more interstices defined by the stent and (b) a distal section extends proximally from the proximal region and is held by the inner surface of the elongate body in a position interposed between the inner surface of the elongate body and an exterior surface of the stent while the stent is in the compressed configuration and (ii) an unrestrained configuration, wherein the distal section of each hook member, while in the restrained configuration, engages the inner surface of the elongate body and is held radially between the stent and the inner surface of the elongate body.

21. The system of claim 20, wherein the one or more hook members comprises a shape memory material.

22. The system of claim 20, wherein at least one of the plurality of hook members is biased to unfurl and disengage the stent when the distal section is advanced out of the elongate member.

23. The system of claim 20, where at least one of the plurality of hook members is preset to unfurl and disengage the stent upon reaching a predetermined temperature.

24. The system of claim 20, wherein at least one of the plurality of hook members extends through the one or more interstices from an interior surface of the stent to an exterior surface of the stent.

25. The system of claim 20, wherein at least one of the one or more hook members extends through the one or more interstices from an exterior surface of the stent to an interior surface of the stent.

* * * * *